(12) United States Patent
Houston et al.

(10) Patent No.: US 6,413,512 B1
(45) Date of Patent: Jul. 2, 2002

(54) COMPOSITION AND METHOD FOR TREATING DISEASE BY INCREASING ACTIVATED $\alpha_2$ MACROGLOBULIN IN THE BLOOD AND EXTRAVASCULAR TISSUE

(75) Inventors: Devin B. Houston, Forsyth; Lynn S. Greaves, Parkville; Lary D. Andrews, Kansas City; Anthony W. Collier, Forsyth, all of MO (US)

(73) Assignee: National Enzyme Company, Forsyth, MO (US)

( * ) Notice: Subject to any disclaimer, the term of this patent is extended or adjusted under 35 U.S.C. 154(b) by 0 days.

(21) Appl. No.: 09/373,329

(22) Filed: Aug. 12, 1999

Related U.S. Application Data

(63) Continuation-in-part of application No. 09/023,847, filed on Feb. 13, 1998, now abandoned.

(51) Int. Cl.[7] .............................................. A61K 38/54
(52) U.S. Cl. ................. 424/94.63; 424/94.2; 424/94.65; 435/212; 435/220; 435/221; 435/222
(58) Field of Search ........................... 424/94.63, 94.65, 424/94.2; 435/219, 220, 221, 222

(56) References Cited

U.S. PATENT DOCUMENTS

| | | | |
|---|---|---|---|
| 3,905,869 A | * | 9/1975 | Hidaka et al. |
| 3,940,478 A | * | 2/1976 | Kurtz |
| 5,223,406 A | * | 6/1993 | Ransberger et al. |
| 5,824,305 A | * | 10/1998 | Mynott |

* cited by examiner

Primary Examiner—Leon B. Lankford, Jr.
(74) Attorney, Agent, or Firm—Mayer, Brown, Rowe & Maw; Joseph A. Mahoney; Thomas R. Stiebel

(57) ABSTRACT

A method for treating various diseases and conditions that are dependent on activated $\alpha_2$ macroglobulin in the blood and extravascular tissue is disclosed. The method comprises orally administering a therapeutically effective amount of protease to a mammal to increase the amount of activated $\alpha_2$ macroglobulin, which in turn enhances the clearance of TNF-$\alpha$, leptin, and $\beta$-amyloid while enhancing delivery of TGF-$\beta$. The protease may be any pharmaceutically acceptable protease, and preferably is of microbial and/or plant origin, given singly or in combination with vitamins, minerals, antioxidants, bioflavonoids, proanthocyanidins, herbs, herbal extracts, plant and animal concentrates, and non-prescription analgesics. The microbial protease is preferably administered in a total daily dosage of at least 100,000 HUT (or equivalent biological activity). The plant protease component is preferably administered in a total daily dosage of at least 50,000 PU (or equivalent biological activity). A composition and method of use thereof for promoting recovery from soft tissue injury is also disclosed. The orally-administered composition contains a mixture of microbial and plant proteases, antioxidant bioflavonoids, proanthocyanidins, vitamins, minerals, plant concentrates and excipients. The composition can also include an analgesic.

20 Claims, 1 Drawing Sheet

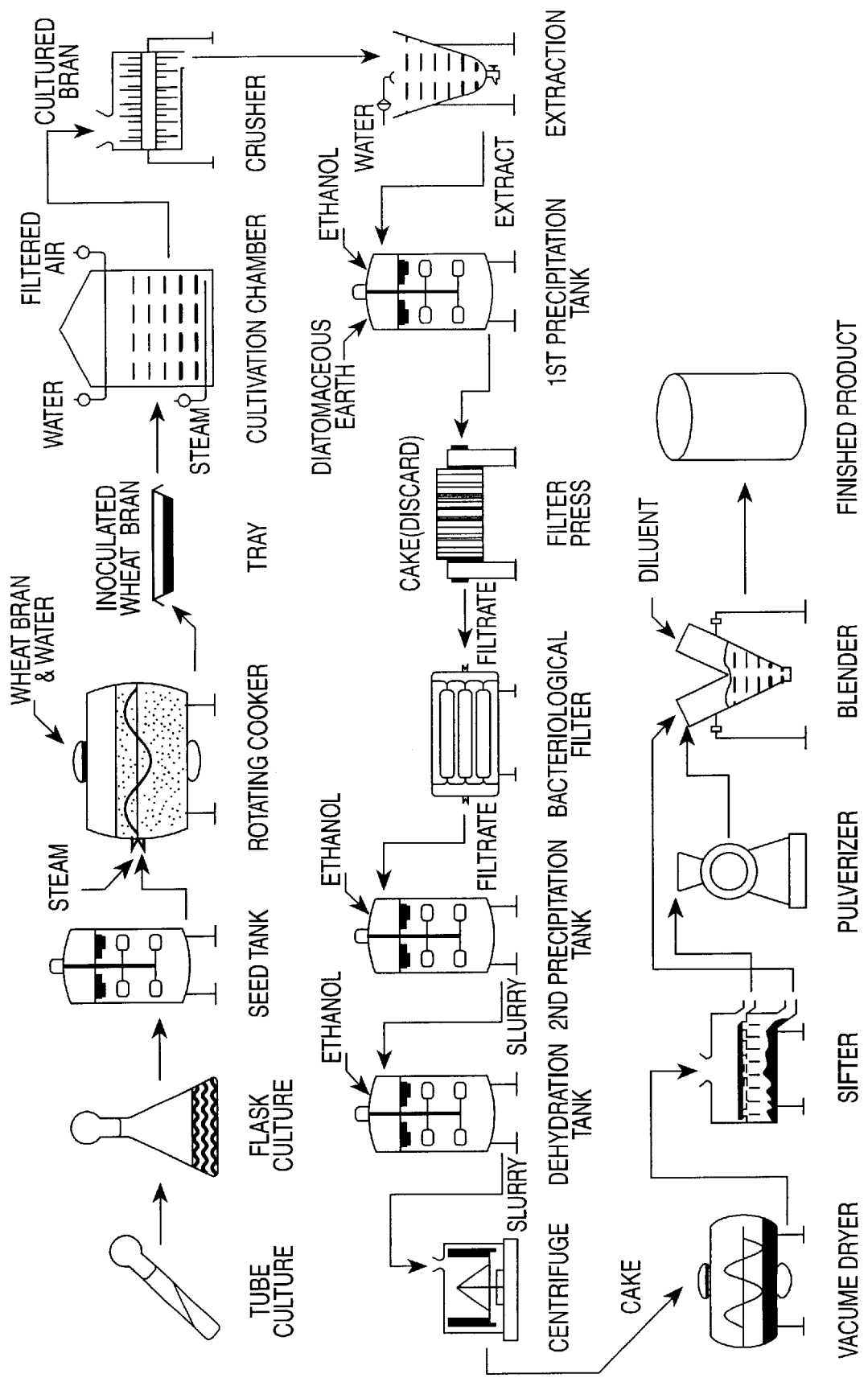

COMPOSITION AND METHOD FOR TREATING DISEASE BY INCREASING ACTIVATED $\alpha_2$ MACROGLOBULIN IN THE BLOOD AND EXTRAVASCULAR TISSUE

RELATED APPLICATION

This application is a continuation-in-part of application Ser. No. 09/023,847, filed on Feb. 13, 1998 now abandoned and assigned to the assignee of the present application.

FIELD OF THE INVENTION

The present invention relates generally to a method of treating human and animal disease utilizing proteolytic enzymes of plant or microbial origin ("proteases" or "proteinases") and, more particularly, to a method of modifying the development or manifestation of conditions affected by the action of biologically-active molecules which may be specifically bound or stimulated by activated alpha-2-macroglobulins. Such biologically-active molecules include, but are not limited to, cytokines and other signaling molecules, such as tumor necrosis factor-alpha (TNF-$\alpha$), leptin, beta-amyloid ($\beta$A), and transforming growth factors (TGF).

BACKGROUND OF THE INVENTION

In many diseases and injuries there is a marked increase in proinflammatory cytokines in the blood. The increased cytokines are believed to contribute to the pathology of the condition. Infection, cancer and tissue injury trigger the production of cytokines. These hormone-like peptides can enter the bloodstream to alter the physiology of distant tissues, or they may behave as paracrine mediators that act only locally. In some disease or injury states, cytokines are beneficial to the host but, in others, cytokines cause the most striking manifestations of the disease (e.g., shock, tissue injury and weight loss). K. J. Tracey, et al., *Tumor Necrosis Factor: A Pleiotropic Cytokine and Therapeutic Target*, Ann. Rev. Med. 45: 491–503 (1994). Proteases and cytokines are intimately interrelated in the body in that cytokines are involved in regulating the production of proteases (Westermarck, J. & Kahari, V. M., *Regulation of Matrix Metalloproteinase Expression in Tumor Invasion*, Faseb J. 13: 781–92 (1999)), and proteases are frequently involved in the liberation of soluble cytokines. Excess circulating proteases also play an important role in the manifestation of disease or injury.

Normal human blood serum contains significant quantities of anti-proteinases, such as alpha-2-macrolobulin ($\alpha$2M), which function to inhibit excess activity of proteases in vivo. $\alpha_2$M has a high molecular weight ($Mr_{human}$=725,000), and is composed of two noncovalently bonded pairs of identical subunits joined by disulfide bonds. Feldman et. al., *Model of $\alpha_2$-Macroglobulin Structure and Function*, Proc. Nat'l. Acad. Sci. USA, 82: 5700–5704 (September 1985). The major source of plasma $\alpha_2$M is the liver (hepatocytes), although other cells including macrophages synthesize and secrete $\alpha_2$M. This may explain the presence of $\alpha_2$M in interstitial sites and malignant tissues. LaMarre et al., *Cytokine Binding and Clearance Properties of Proteinase-Activated $\alpha_2$-Macroglobulins*, Lab. Investigation 65(1):3–14 (1991). $\alpha_2$M inhibits proteinases of all four (4) catalytic classes. Barrett et al., *The Interaction of $\alpha_2$-Macroglobulin With Proteinases: Characteristics and Specificity of the Reaction, and a Hypothesis Concerning its Molecular Mechanism*, Biochem. J. 133: 709–724 (1973); Harpel et al., *Studies on Human Plasma $\alpha_2$-Macroglobulin-Enzyme Interactions*, J. Exp. Med. 138: 508–521 (1973); Salveson et al., *Covalent Binding of Proteases in Their Reaction With $\alpha_2$-Macroglobulin*, Biochem. J. 187: 695–701 (1980). Proteinases inhibited by $\alpha_2$M include the coagulation proteinases thrombin and Factor Xa, the fibrinolytic enzymes urokinase-type and tissue-type plasminogen activators as well as plasmin, kallikrein of the contact system, the neutrophilic proteinases elastase, cathepsin G, and collagenase, and several bacterial proteinases. DeBoer et al., *Alpha-2-Macroglobulin Functions as an Inhibitor of Fibrinolytic, Clotting, and Neutrophilic Proteinases in Sepsis: Studies Using a Baboon Model*, Infection and Immunity 61(12): 5035–5043 (1993).

Because of the biological importance of activated $\alpha_2$M ($\alpha_2$M*) scavenging of proteinases, several laboratories have attempted to elucidate the structure and function of $\alpha_2$M. The trap mechanism and structure identified by Feldman et al. has been generally accepted. According to the "trap" hypothesis, proteinases cleave specific peptide bonds within the "bait" amino acids sequence of the $\alpha_2$M subunits and become entrapped within the interior of the $\alpha_2$M as a result of its conformational change. Feldman et. al., supra at 5701. Methylamine mimics the proteinase-induced conformational changes by reacting with the $\alpha_2$M thiol ester bonds, and has therefore been commonly used in studies of $\alpha_2$M*.

A substantial body of research has established that $\alpha_2$M* complexes acquire a high affinity for binding proinflammatory cytokines, resulting in their removal from the body along with the protease bound in the $\alpha_2$M* complex. Activated $\alpha_2$M has been shown to play a pivotal role in regulating inflammatory and homeostatic mechanisms of disease and injury by binding major mediators such as tumor necrosis factor-alpha (TNF-$\alpha$), transforming growth factor-$\beta$1 (TGF-$\beta$1), transforming growth factor-$\beta$2 (TGF-$\beta$2), basic fibroblast growth factor (bFGF), platelet derived growth factor (PDGF), nerve growth factor (NGF), interleukin-1$\beta$(IL- 1$\beta$) and interleukin-6 (IL-6). Wolleberg et.al., *Binding of Tumor Necrosis Factor Alpha to Activated Forms of Human Plasma Alpha$_2$Macroglobulin*, Amer. J. Path., 138 (2): 265–272 (1991). Recent research suggests that various proinflammatory cytokines, and especially TNF-$\alpha$, play a major role in rheumatoid arthritis. M. Feldmann, et at., *Role of Cytokines in Rheumatoid Arthritis*, Ann. Rev. Immun., 14: 397–440 (1996).

One of the hallmarks of most disease processes is acute inflammation, which features the release of neutrophil-derived oxidants. It has recently been shown that "oxidation serves as a switch mechanism that down-regulates the progression of acute inflammation by sequestering TNF-alpha, IL-2, and IL-6, while up-regulating the development of tissue repair processes by releasing bFGF, beta-NGF, PDGF, and TGF-beta from binding to alpha2M." Wu, Patel & Pizzo, *Oxidized Alpha2-Macroglobulin (alpha2M) Differentially Regulates Receptor Binding by Cytokines/Growth Factors: Iimplications for Tissue Injury and Repair Mechanisms in Inflammation*. J. Immunol. 161: 4356–65 (1998). The conformationally modified or "activated" $\alpha_2$M is rapidly cleared from the circulation as it more readily binds to specific cell-surface receptors on hepatocytes, macrophages, and fibroblasts and undergoes receptor-mediated endocytosis. These cellular receptors rapidly clear $\alpha_2$M-protease and $\alpha_2$M-methylamine complexes from the systemic circulation, primarily in the liver. Native $\alpha_2$M, on the other hand, is not receptor recognized and has a prolonged half-life in circulation.

Activated $\alpha_2$M is believed to also play a role in the mediation and regulation of leptin. Leptin is a 16kDa polypeptide consisting of 167 amino acids that is expressed and secreted from adipose tissue under the control of the "obese gene." Zhang Y, et al., *Positional Cloning of the Mouse Obese Gene and its Human Homologue*, Nature, 372:425–432 (1994). Murine studies indicate that leptin acts on the CNS to regulate body weight through the control of appetite and energy expenditure. Pelleymounter M A., et al., *Effects of the Obese Gene Product on Weight Regulation in ob/ob Mice*, Science, 269:540–43 (1995). Leptin has also been shown to affect sympathetic nerve activity, insulin resistance, and renal sodium excretion. Haynes W G, et al., *Cardiovascular Consequences of Obesity: Role ofLeptin*, Clin. Exp. Pharm. Physiol., 25:65–69 (1998). Obesity is associated with increased activity of the sympathetic nervous system and, therefore, there appears to be a causal link between excess leptin and other systemic, and especially cardiovascular consequences of obesity. See id.

There are a variety of undesirable consequences of obesity, including insulin resistance, dyslipoproteinemia, and hypercoagulability, all of which are probably due to increases in circulating TNF-$\alpha$ and leptin. Halle M. et al., *Importance of TNF-alpha and Leptin in Obesity and Insulin Resistance: A Hypothesis on the Impact of Physical Exercise*, Exerc. Immunol. Rev. 4:77–94 (1998). Activated $\alpha_2$M has been identified as a leptin binding factor in human plasma. Thus, the binding of leptin to activated $\alpha_2$M and its rapid clearance by the $\alpha_2$M receptor can significantly influence the bioavailability of leptin. Birkenmeier G., et al., *Human Leptin Forms Complexes with $\alpha_2$-Macroglobulin Which are Recognized by the $\alpha_2$-Macroglobulin Receptor/Low Density Lipoprotein Receptor-Related Protein*, Eur. J. Endocrin., 139:224–230 (1998).

TNF-$\alpha$ is thought to be a modulator of gene expression in adipocytes and is implicated in the development of insulin resistance and obesity. Thus, the clearance of TNF-$\alpha$ by activated $\alpha_2$Ms also appears desirable. Fernandez-Real J M, et al., *The TNF-alpha Gene NCO I Polymorphism Influences the relationship Among Insulin resistance, Percent Body Fat, and Increased Serum Leptin Levels*, Diabetes 46(9):1468–72 (1997). The Fernandez-Real group found that increasing transcription of TNF-$\alpha$ using a polymorphism on the TNF-$\alpha$ gene increased serum leptin concentrations in a sample of human subjects. Similarly, diet-induced weight loss reduced TNF-$\alpha$ expression and serum leptin levels and improved insulin sensitivity and lipid metabolism. Halle M. et al., *Importance of TNF-alpha and Leptin in Obesity and Insulin Resistance: a Hypothesis on the Impact of Physical Exercise*, Exerc. Immunol. Rev. 4:77–94 (1998). A composition that activates $\alpha_2$Ms can also be useful for the treatment of non-insulin dependent diabetes and insulin-resistance effect (See Morimoto et al., *Life Science*, 61:795–803 (1997)), Crohn's disease (See U.S. Pat. No. 5,656,272) and cachexia (See Tisdale, *Wasting and Cancer*, J. Nutrition, 129 (1S Suppl.): 243S–246S.

Activated $\alpha_2$Ms also affect the clearance of beta-amyloid ($\beta$A). Studies show that increased deposition and aggregation of $\beta$A is one of the principal neuropathological features of Alzheimer's disease (AD). Selkoe D J, *Cell Biology of the Amyloid $\beta$-Protein Precursor and the Mechanism of Alzheimer's Disease*, Ann. Rev. Cell Biol., 10:373–403 (1994). Amyloid deposits comprise a 39–43 amino acid peptide(s), which is a proteolytic processing product of the amyloid precursor protein (APP), that is expressed by most, if not all, cells. Once formed, the $\beta$A peptide oligomerizes and aggregates into insoluble fibrils that are directly toxic to neurons. Pike C. J., et al., *In- Vitro Aging of $\beta$-Amyloid Protein Causes Peptide Aggregation and Neurotoxicity*, Brain Res., 563:311–314 (1991). It has been found that the circulating or brain concentration of $\beta$A in patients with AD is greater than normal patients, and it is believed that factors contributing to $\beta$A catabolism and/or clearance of $\beta$A may contribute to either diffuse (preamyloid) or neuritic (senile) plaques in the brain. Van Gool D., et al., *$\alpha_2$-Macroglobulin Expression in Neuritic-Type Plaques in Patients with Alzheimer's Disease*, Neurobiol. Aging, 14:233–37 (1993).

Using radiolabeled $\beta$A, Du et al. found that $\alpha_2$M binds to $\beta$A with high affinity. Du Y, et al., *$\alpha$2-Macroglobulin as a $\beta$-Amyloid Peptide-Binding Plasma Protein*, J. Neurochem., 69:299–305 (1997). This indicates that $\beta$A is cleared from the brain by conjugation with $\alpha$2M and endocytosis of the $\beta$A/$\alpha$2M complex by low-density lipoprotein receptor-related protein (LRP). Investigations found that $\alpha_2$M in AD brain were localized to neuritic plaques and that $\alpha_2$M receptors, or LRP, were concentrated in brain areas affected by AD. Strauss S., *Detection of Interleukin-6 and $\alpha$2-Macroglobulin Immunoreactivity in Cortex and Hippocampus of Alzheimer's Disease*, Lab. Invest., 66:223–230 (1992).

It has also been discovered that activated $\alpha_2$M directly stimulates macrophages. See Misra & Pizzo, *Ligation Of The Alpha2 Signaling Receptor With Receptor-Recognized Forms Of Alpha2-Macroglobulin Initiates Protein And DNA Synthesis In Macrophages: The Effect Of Intracellular Calcium*. Biochim. Biophys. Acta.,1401:121–8 (1998). Such macrophage stimulation can have beneficial effects such as fighting bacterial infection.

Despite the growing body of research implicating $\alpha_2$M* as a mediator of various diseases, pharmacotherapy has failed to address modulating $\alpha_2$M to effect treatment of the diseases. In particular, the prior art has failed to focus on modulating $\alpha_2$Ms with agents that are effective, well tolerated by most patients and economical to use. Most current therapy is directed to altering the function of the cytokines themselves. For example, EMBREL, the commercial product based on Le et al. U.S. Pat. No. 5,698,195, *Methods of Treating Rheumatoid Arthritis Using Chimeric Anti-TNF Antibodies* issued Dec. 16, 1997, teaches the use of anti-TNF antibodies specific for human tumor necrosis factor-alpha for the treatment of rheumatoid arthritis. Such treatment, however, has the disadvantages of being expensive at approximately $220.00 per week of therapy and is administered by injection and therefore carries the associated risks.

Additionally, Mynott U.S. Pat. No. 5,824,305 focuses on a different mechanism and teaches a method of treating diseases mediated by cyclic nucleotide pathways with purified stem bromelain protease.

Activated $\alpha_2$Ms play a key role in influencing the availability and activity of various peptides to specific cells and, therefore, influencing cellular physiology. Consequently, there is a definite need in the art of mammalian therapeutics for a pharmacological agent that increases the activated or "fast" form of $\alpha_2$M to mediate the effects of the above-mentioned cytokines and other signaling molecules, has a low side effect profile, and is economical to use.

SUMMARY OF THE INVENTION

In accordance with the present invention, it has now been discovered that certain manifestations of disease and injury may be effectively treated with a mixture of proteases of microbial and/or plant origin. Specifically, exogenous proteases are useful for increasing activated alpha-2-macroglobulin in the blood and extravascular tissue. Such proteases are preferably administered orally, either singly or in combination with synergistic ingredients, in the form of capsules (hard and soft), tablets (film coated, enteric coated or uncoated), powder or granules (film coated, enteric coated or uncoated) or liquid (solution or suspension) in an amount to produce the desired pharmacological effect, namely objective improvement of the condition of treated patients by positively influencing the cellular physiology.

The protease may be any pharmaceutically acceptable protease, and preferably is of microbial and/or plant origin, given singly or in combination with vitamins, minerals, antioxidants, bioflavonoids, proanthocyanidins, herbs, herbal extracts, plant and animal concentrates, and analgesics. The microbial protease is preferably administered in a total daily dosage of at least 100,000 HUT (or equivalent biological activity). The plant protease is preferably administered in a total daily dosage of at least 50,000 PU (or equivalent biological activity).

A specific composition and method of use thereof for promoting recovery from soft tissue injury is also disclosed. The orally-administered composition contains a mixture of microbial and plant proteases, antioxidant bioflavonoids, proanthocyanidins, vitamins, minerals, plant concentrates and excipients. The composition can also include an analgesic.

It is, therefore, an object of the present invention is to treat mammalian disease or injury manifested by cytokines and other signaling molecules by administering to a mammal oral doses of protease to increase activated $\alpha_2 2M^*$ in the serum, which in turn serves as a biological response modifier for the disease or injury. The present invention can be employed to treat any disease or injury where activated $\alpha_2 M^*$ play a role.

It is another object of the present invention to supply exogenous protease to the circulation to create a "preemptive" increase in $\alpha_2 M^*$ capable of binding proinflammatory cytokines and thereby interrupting cytokine-induced pathology.

It is also an object of the present invention to provide a protease-based composition and method for decreasing the time required for healing of soft tissue injuries resulting from accidents, sports injuries, various surgical procedures and the like.

It is yet another object of the present invention to treat disease or injury with a composition that is easy to administer, economical and well-tolerated by patients.

BRIEF DESCRIPTION OF THE DRAWINGS

FIG. 1 is a diagram of the production process used to produce the proteases used in the present invention.

DETAILED DESCRIPTION OF THE INVENTION

Before the present compositions and method of use thereof for increasing activated $\alpha_2 M$ are disclosed and described, it is to be understood that this invention is not limited to the particular configurations, compositions, process steps, and materials disclosed herein as such configurations, compositions, process steps, and materials may vary. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to "an antioxidant" includes a mixture of two or more antioxidants, reference to "a vitamin" includes reference to one or more of such vitamins, and reference to "a microbial protease" includes references to two or more of such microbial proteases.

As used herein, "effective amount" means an amount of a composition according to the present invention that is nontoxic but sufficient to provide the selected local or systemic effect and performance at a reasonable benefit to risk ratio attending any product of this nature. An effective amount of an analgesic is an amount sufficient to provide a selected level of pain relief.

As used herein, "acceptable salts" means salts of, for example, citric acid or ascorbic acid, wherein such salts are generally regarded as safe for human consumption.

In general, the present invention is directed to a method for alleviating the manifestations of mammalian disease or injury by administering an effective amount of a mixture of proteolytic enzymes (proteases) derived from microbial and/or plant origin. The method of the present invention may be used to treat any type of cytokine or signaling peptide-mediated disease or injury whereby the proteases serve as high affinity biological response modifiers through their activation of alpha-2-macroglobulins to either enhance the clearance of the particular cytokine or signaling molecule such as TNF-$\alpha$, leptin, beta-amyloid, and interleukins, or to enhance the delivery to a particular tissue of a particular cytokine or signaling molecule including transforming growth factors, basic fibroblast growth factor, platelet derived growth factor, and nerve growth factor. Diseases and injuries treated by the present invention include rheumatoid disease, excess weight including obesity, cachexia, hypertension and cardiovascular disease, dyslipoproteinemia, insulin resistance, non-insulin dependent diabetes, Crohn's disease, dementia of the Alzheimer's type, infections and soft tissue injuries including surgery.

Cytokines play a major role in the manifestation of inflammation, which is a predominant biological reaction to a myriad of injurious agents and events. It is well-known that host defensive and reparative processes in inflammation can be inimical to the body's welfare. Common characteristics of inflammation are bruising, swelling and pain. The body's defensive mechanisms can bring about the release of products toxic to the host or destruction of some of its tissues. Additional detrimental consequences of inflammation include fibrin deposition and reduction in vascularity causing changes in tissue permeability creating additional morphologic barriers to the penetration of antibodies or pharmacological agents into the injured area. Some of the autolysis products released by tissue necrosis often constitute a good medium for microorganisms and can even antagonize the antimicrobial activity of many pharmaceutical agents, thereby exacerbating the injury and prolonging the recovery process.

Current drug treatment for inflammatory conditions that incorporate steroids and NSAIDs is aimed at complete inhibition of inflammation. The goal of using orally-administered proteases in treating soft-tissue injury is to minimize, not inhibit, the inflammatory process by accelerating the normal healing process. Undesirable side effects from the use of steroids and NSAIDs dictate a need for safer, but still effective, alternatives for inflammation relief. The method and compositions of this invention are directed to provide this relief without the adverse side effects.

Other measures aimed solely at the etiologic agent will often prove inadequate. On the other hand, a therapeutic agent directed at the host response level and capable of modifying defensive and reparative processes of localized inflammation without depriving the body of its benefits would prove invaluable. The method and compositions of this invention rely upon the ability of orally-administered proteases to activate $\alpha_2$Ms to minimize the detrimental effects of proinflammatory cytokines.

In a disease and injury free state, mammals have very little circulating protease in the blood. Circulating $\alpha_2$M, on the other hand, is abundant in human plasma (~2ng/ml), and has a major function of non-specifically binding protease. Applicants demonstrate that the exogenous administration of proteases increases the amount of activated $\alpha_2$M in the blood and extravascular tissue, which enhances the clearance of the cytokine or signaling molecule of interest minimizing its detrimental actions, and thereby having highly desirable therapeutic effects.

A reduction of circulating TNF-$\alpha$, leptin and $\beta$A is beneficial to patients with rheumatoid and cardiovascular diseases, obesity, and plaque deposition associated with Alzheimer's disease, respectively. The elevation of activated $\alpha_2$M/TGF-$\beta$complexes also improves wound healing by delivering the activated TGF-$\beta$ where it is most beneficial for tissue repair.

The absorption of orally-administered proteases in animals and humans has been extensively studied. The prevailing finding of these studies is that proteases can be partially absorbed intact, with activity preserved, from the digestive tract and subsequently distributed systemically in the blood. This is evidenced by anecdotal observations of the systemic action of oral protease supplementation and also well-controlled studies demonstrating that proteins, including proteolytic enzymes, can be detected in the circulation in active whole form after oral administration. Castell J. V., Friedrich G., Kuhn C. S. & Poppe G. E., *Intestinal Absorption Of Undegraded Proteins In Men: Presence Of Bromelain In Plasma After Oral Intake*, Am. J. Physiol., 273: G139–G146 (1997).

The discovery of the beneficial effect of protease on modulating biological functions such as inflammation and tissue repair has inspired considerable experimentation into exogenous sources and their clinical effects. The most common source of exogenous proteases used for inflammation is the pancreas of pigs and cows slaughtered for meat, commercially known as pancreatin. Pancreatin contains such proteases as trypsin, chymotrypsin, carboxypeptidase, and elastase. Plant sources of protease, primarily bromelain derived from pineapple, and papain derived from papaya, are the second most studied exogenous sources of proteases for inflammation. Proteases from microbial sources, such as fungi and bacteria, are relative newcomers as therapeutic agents for inflammation.

Animal, plant and microbial proteases have been found to differ significantly in their molecular weight, molecular configuration, substrate specificity, kinetic reactions, pH and temperature reaction optima, inhibitors, cofactors and composition of the proteolytic active site.

S. Schwimmer, *Source Book for Food Enzymology*, p.89–122 (1981). For example, animal enzymes optimally digest food in the more alkaline pH of the small intestines whereas microbial enzymes work better in a much lower pH. Such differences in functional properties do not support the assumption that all proteolytic enzymes will share common properties in terms of systemic absorption, distribution, and physiological action.

Early in the study of proteases, it was observed that the administration of animal-derived proteases could accelerate the healing of an inflamed site. Therefore, a large database exists of clinical results from orally-administered, animal-derived proteases establishing the effectiveness of these proteases as therapeutic agents for inflammatory conditions. However, a clear mechanism of physiological action for animal-derived proteases is yet to be determined. The same is true for plant-derived proteases. Plant proteases have been found to have a positive effect on inflammation but only one mechanism of action for bromelain has been proposed and supported by research. See U.S. Pat. No. 5,824,305. The largest body of evidence supporting the use of protease for inflammatory conditions studied the effects of a mixture of papain, bromelain, trypsin, chymotrypsin, pancreatin and rutin. In most cases, the mixture was in addition to standard medical care. It must also be noted that a large quantity of the mixture was required to observe beneficial results, sometimes as many as 30 tablets per day.

The present invention offers improvements over prior proteolytic products in that, unlike other protease compositions, the primary benefit is obtained from the use of a protease combination derived from microbial sources whose mechanism of action and dosing regimen are defined. These microbial proteases have been extensively used over the past 40 years in the food industry to improve the taste, texture or solubility of certain foods but their effectiveness as mediators of disease and injury is the focus of this invention. The combination of microbial proteases with plant proteases and other synergistic ingredients in this invention serve to improve the effectiveness of the inventive compositions.

The broad range of physiological action and greater biological activity per gram of microbial proteases present in the invention means only a few capsules are required for the desired clinical effect compared to the large dosage required for animal and plant-derived protease products. Because of the high potency provided by microbial enzymes, the amount of plant proteases in this invention can be reduced significantly compared to known compositions. The invention does not contain animal-derived products and, thus, is acceptable to patients who may object to the ingestion of animal products.

Since three significant goals of the present invention are ease of administration, low cost to the user, and minimal side effects, it is important that the composition and method employed to obtain the proteases is relatively economical and results in pure (hypoallergenic), highly concentrated preparations. Use of microbial proteases in the present invention satisfies all three criteria. A preferred method for producing microbial proteases from various species of Aspergillus fungi is solid state fermentation illustrated diagrammatically in FIG. 1, although other production methods known in the art are also acceptable. Referring to FIG. 1, the fermentation process begins by taking a population of the desired fungi from a test tube culture and transferring it to a large flask for additional growth. This cultured fungi is then moved to a seed tank where it is further propagated. The resulting concentrated suspension of fungi is then transferred to a rotating cooker and mixed with sterilized koji (wheat or rice bran), water and steam where it is cooked for a sufficient period of time to inoculate the koji with fungi. The inoculated koji is then moved onto large trays, which are then transported to a cultivation chamber where the fungi are permitted to grow. Fermentation under controlled temperatures and humidity conditions may take from a few days to a week or more to complete.

At the conclusion of fermentation, the cultured koji is then transferred to a crusher device, which pulverizes the koji mash. The resulting pulverized mash is then moved to an extractor to filter the particulate matter from the slurry. For some processes, there may also be microfiltration or ultra-filtration steps to concentrate the aqueous enzymes before precipitation. The slurry is then moved to a first precipitation tank where it is mixed with ethanol and filtered through diatomaceous earth and then run through a filter press where the cake is discarded. The filtrate from the filter press is then processed through a bacteriological filter before it is moved to a second precipitation tank for further filtering and precipitation. The ethanol precipitation and bacteriological filter steps produce enzymes that are microbially very "clean" i.e., they have very low microbes when compared to other food products such as fluid or pasteurized milk. The slurry is then centrifuged and the resulting cake is transferred to a vacuum dryer for drying. The dried proteinaceous material is then passed through a sifter and then a pulverizer to reduce the particle size. This material is then placed in a blender and diluent may or may not be added to standardized the potency of the finished powder product.

In accordance with the present invention, the proteolytic enzymes are administered orally in daily dosages in the form of a pharmaceutical composition comprising mixtures of about at least 100,000 HUT (or equivalent biological activity) of microbial proteases, and/or mixtures of about 50,000 PU (or equivalent biological activity) of plant proteases.

The present composition of the invention employs the dosage unit designations HUT (Hemoglobin Unit Tyrosine) and PU (Papain Units), which are Food Chemical Codex activity units to describe the preferred potencies of the proteolytic enzymes. One skilled in the art will recognize that there are many different activity unit designations used for microbial and plant proteases depending upon the type of application and geographic location of the enzyme supplier. However, regardless of the activity unit designation employed, equivalent biological activity can be determined by readily available laboratory analysis.

The dose is intended to be administered on an empty stomach (i.e., at least two hours after a meal or snack or one hour before a meal or snack). The dose administered to a mammal, particularly a human, in the context of the present invention should be sufficient to effect a therapeutic response in a reasonable timeframe. The dose and timing of the dose will be determined by the strength of the particular composition administered and by the condition of the person, as well as the body weight of the person to be treated. The size of the dose also will be determined by the existence, nature and extent of any adverse side effects that might accompany the administration of a particular composition. The formulations described herein may be administered concurrently with other necessary medications. For example, they may be administered together with non-steroidal anti-inflammatory agents or the more recent cyclooxygenase-2 (COX-2) inhibitors in the treatment of arthritis.

The composition of the present invention may also include additional ingredients such as other enzymes, vitamins, minerals, antioxidants, bioflavonoids, proanthocyanidins, herbs, herbal extracts, plant and animal concentrates and analgesics. Preferably, the composition additionally comprises a pharmaceutically acceptable carrier. Pharmaceutically-acceptable carriers are also well-known to those who are skilled in the art. The choice of carrier will be determined, in part, both by the particular composition and by the particular method used to administer the composition. One skilled in the art will appreciate that suitable methods of administering the protease-based formulations of the present invention to a mammal are available and, although more than one method can be used to administer a particular composition, a particular method can provide a more immediate and more effective reaction than another. There is a wide variety of suitable forms of administration of the pharmaceutical compositions of the present invention.

The preferred forms of administration in the present invention are oral forms know in the art of pharmaceutics. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

A preferred embodiment of the present invention is a composition comprising a mixture of proteases from microbial and plant sources combined with vitamin C, bioflavonoids, proanthocyanidins, calcium and mineral-rich algae. The preferred microbial protease composition is comprised of a mixture of proteolytic enzymes from *Aspergillus oryzae, Aspergillus niger, Aspergillus sojae, Aspergillus flavus, Aspergillus awamori, or Bacillus subtilis*. The use of microbial proteases in this formulation as anti-inflammatory agents and promoters of wound healing constitutes an improvement upon known compositions for these purposes. The microbial portion of this composition is comprised of three fungal protease derived from strains of Aspergillus and one bacterial protease derived from *Bacillus subtilis*. All of these microbial proteases are commercially derived either by the methodology previously described or by other published methods, see, e.g., S. Schwimmer, *Source Book of Food Enzymology*, p. 89–122 (Avi Publishing, 1981), and provide a wide range of enzymatic activities. The predominant characteristics of the microbial protease mixture is a pH optimum for activity in the range of 5.0 to 9.0, which corresponds generally to the physiological pH of 7.4, and broad substrate specificity, with a slight preference for cleaving the carboxyl side of hydrophobic amino acid residues. In addition, one of the microbial proteases provides endopeptidase activity and exopeptidase activity observed as preferential cleavage of leucide residues from the amino terminus of peptides. Another microbial protease is advantageous for its stability at a pH as low as 2.0.

The microbial proteases used in the present composition are complementary in that they provide overlap in pH optima, substrate specificity, and mode of cleaving the peptide backbone of proteins. Unlike many other types of proteins, these proteases are more stable in the presence of stomach acid and, therefore, are less likely to be destroyed by the process of digestion. The proteolytic activity of human serum has been observed to increase after ingestion of protease-containing preparations, indicating gastric survival of proteases. Of the total quantity of enzymes ingested, approximately 10% to 40% are absorbed into the general circulation. The molecular weight of microbial protease is about 35 Kda. The broad range of physiological conditions under which these proteases remain active is necessary, since microenvironmental conditions within the body may include pH values much different than 7.4, the norm for human serum.

It is also preferred that the mixture of proteases in the preferred embodiments include plant-derived proteases, such as bromelain and papain. Bromelain is the collective name for the proteolytic enzyme composition derived from the stem of the pineapple plant, *Ananas comosus*. Papain is purified from the fruit of the tropical melon tree, *Carica papaya*. The primary use of highly concentrated microbial proteases in the present preferred embodiment has allowed a relatively small portion of the composition to be comprised of plant proteases. This is advantageous because the plant sources of both bromelain and papain are subject to environmental influences, which can have a significant impact upon the commercial availability and price of both plant enzymes.

Bromelain and papain are referred to as thiol proteases and contain a cysteine residue at the active site. Under oxidizing conditions, such as inflammation, the thiol group of this cysteine loses a hydrogen atom and may crosslink with another thiol group, forming a disulfide bridge or, alternatively, crosslinking with another residue through the same oxidative process. In this oxidized state, the bromelain and papain lose activity. The present composition solves this problem through the inclusion of antioxidant vitamin C, bioflavonoids and proanthocyanidins that prevent the oxidation of the active sulfhydryl group of the thiol proteases.

Bromelain and Papain have been studied more extensively than the microbial enzymes and possess potent anti-inflammatory properties. The known proteolytic enzymes of bromelain and papain share a high degree of amino acid sequence homology around the active center, and evidence suggests that bromelain and papain use the same catalytic mechanism. Bromelain differs from papain, however, in having a different specificity of cleavage. In addition, the known proteolytic enzymes of bromelain are glycoproteins, whereas, papain is a simple protein. See U.S. Pat. No. 5,767,066; Taussig et. al., J. Ethnopharmacol., 22:191–203 (1988). Research has established that bromelain is absorbed in an intact, functional state into human circulation. Castel et. al. *Intestinal Absorption of Undegraded Proteins in Men: Presence of Bromelain in Plasma After Oral Intake*, Am. J. Physiol., 273:139–46 (1977). The molecular weight of bromelain is approximately 24–26 Kda.

Microbial proteases have different active sites and are not labile under oxidative conditions. By focusing on microbial proteases in the preferred embodiments of the invention, the stability of the proteolytic activity of the composition is greatly improved thus providing superiority over known compositions that relied solely or primarily upon the actions of the plant thiol proteases, bromelain or papain.

Vitamin C (ascorbic acid), a bioessential organic acid, is included in a preferred embodiment because it is well known as an antioxidant, is essential in the biosynthesis of collagen, and for supporting immune function, thereby improving the healing of damaged tissues. Vitamin C is provided in the composition in the form of calcium ascorbate, which is a buffered form of ascorbic acid. A preferred embodiment also contains other potent antioxidants in the form of bioflavonoids and proanthocyanidins. The bioflavonoid, quercetin (3.3',4',5,7-pentahydroxyflavone), has been shown to inhibit certain mediators of the inflammatory process, and another bioflavonoid, rutin (3-rhamnoglucoside of 5,7,3',4'-tetrahydroxyflavonol), has been shown to reduce chemically-induced inflammation in clinical studies. Research has shown that the active antioxidants in grape extract, known as proanthocyanidins, are anti-inflammatory agents capable of inhibiting the process of edema.

It is also preferred that the presently described composition includes calcium and trace minerals for use in homeostatic functions, in musculoskeletal healing, as electrolytes and as enzyme cofactors. Calcium is provided in the present preferred embodiment as calcium citrate and calcium ascorbate because the mineral is optimally absorbed by the body from these two forms. Clinical experience with high doses of orally-administered microbial protease has resulted in muscle cramping in some patients. The $\alpha_2$M-protease complexes have been shown to cause a release of intracellular calcium (Misra et al., Biochem. J. 15:885–91 (1993)), which is a cause of cramping. Oral administration of calcium in conjunction with microbial protease has alleviated the cramping. The trace minerals in the present preferred embodiment are provided by mineral-rich algae such as marine kelp, Laminaria sp., and Irish moss, *Chondrus crispus*.

The present preferred embodiment may also contain an effective amount of a non-prescription or prescription analgesic, such as acetaminophen, ibuprofen, ketoprofen, salicylates such as acetylsalicylic acid (aspirin), and indomethacin. Dosages of such analgesics should not exceed federal regulations. In accordance therewith, a preferred dosage range for acetaminophen is from about 65 mg. to 390 mg. per dosage unit.

The composition of the present preferred embodiment is orally administered in capsule (hard or soft), tablet (coated or uncoated), powder or granule (coated or uncoated) or liquid (solution or suspension) form and dissolves easily in the stomach. One skilled in the art will perceive other physical forms of the composition that will be equally as useful. The composition may optionally include production aids or excipients. In the preferred embodiment, the composition is prepared by blending together the stated raw materials in an agglomerator so as to result in a product having a uniform composition with the proportions of the components as indicated. The agglomerated material is then placed in gelatin or other capsules, pressed into tablets, dissolved or suspended in liquid, or packaged in a suitable container.

The formula, per dosage unit, of a preferred embodiment is as follows:

| | |
|---|---|
| Microbial Proteases | 20,000 HUT to 550,000 HUT (or biological equivalents) |
| Plant Proteases | 80,000 PU to 1.5 million PU (or biological equivalents) |
| Ascorbic Acid (from Calcium Ascorbate) | 15 mg. to 100 mg. |
| Bioflavonoids (Rutin and Quercetin) | 15 mg. to 100 mg. |
| Proanthocyanidins (Grape Extract) | 2 mg. to 15 mg. |
| Calcium (from Calcium Citrate and Calcium Ascorbate) | 5 mg. to 150 mg. |
| Trace Mineral-Rich Algae | 40 mg. to 200 mg. |

A dose is intended to be administered on an empty stomach (at least two hours after a meal or snack and one hour before a meal or snack) five times per day. A dose will be determined by the strength of the particular composition administered and by the condition of the person, as well as the body weight of the person to be treated. The size of a dose also will be determined by the existence, nature and extent of any adverse side effects that might accompany the administration of this composition. Additionally, dosage forms comprising only proteases in the ranges noted above may be employed.

The present invention will be further illustrated by the following examples that are not intended to limit the scope of the invention.

EXAMPLE 1

Groups of CF1 mice will be injected intraperitoneally (i.p.) with preformed protease-alpha-2-macroglobulin complexes, preformed methylarnine-alpha-2-macroglobulin complexes or bovine serum albumin only. Fifteen minutes later doses of either recombinant tumor necrosis factor-alpha or interferon gamma will be injected i.p. It is hypothesized that a significant reduction in circulating cytokine levels will be observed in the mice that receive protease and methylamine-activated alpha-2-macroglobulins relative to the placebo.

EXAMPLE 2

Adult CF1 mice will be challenged with bacterial endotoxic lipopolysaccharides (LPS) to induce a rapid increase in circulating levels of acute-phase proteins and cytokines, including tumor necrosis factor-alpha and interferon-gamma. Mice challenged with LPS will be injected with protease, preformed protease-alpha 2-macroglobulin complexes, preformed methylamine-alpha 2-macroglobulin complexes, or vehicle only. It is postulated that significant reductions in circulating cytokine levels will be observed in all three treatment groups compared to the control group.

EXAMPLE 3

Two females were admitted for treatment of varicose veins. Treatment was to consist of injection of sodium morrhuate, a sclerosing agent, into the affected veins of each leg. One leg was to be treated at each visit with the visits separated by one month. This particular procedure lent itself well for study, as one leg could be used as the control (normal post-operative treatment) and the other as the dependent variable (normal post-operative treatment plus the protease-based composition). Follow-up visits were made at one, two and four weeks after each procedure. The first leg was treated with standard medical care. At the week-one follow-up examination, the injected vessels were observed to be clotted and palpable. The more superficial vessels contained dark blue clots. Upon palpation of the vessels, a noticeable amount of pain was reported by both patients. At two weeks post-procedure, tissue bruising extended up to 3 mm on either side of the sclerosed vessel. Skin discoloration had changed from dark blue to yellow-green. The larger sclerosed vessels were still palpable but no longer painful. At four weeks post-procedure, bruising was apparent only in the largest vessels. The surrounding skin had a brown appearance that was due to staining by hemosiderin, a breakdown product of blood hemoglobin. The second leg was treated in a similar manner with the exception that the protease-based composition according to the present invention was added to the treatment regimen. The patients took the composition immediately after the procedure and four days following. The week-one post-procedure examination revealed bruising in only 50% of the vessels treated, and complete clearance of clots from 25% of the smaller superficial vessels. Pain was present over the largest vessels only upon deep palpation. Two weeks after treatment, 80% of all bruising and discoloration had resolved, and in the remaining areas only yellow-green bruising was observed. At four weeks after treatment, all bruising was resolved and no brown hemosiderin staining was noted. Both patients stated that they had fewer subjective problems following the second procedure.

EXAMPLE 4

A 35-year-old male underwent lipoplasty of the right and left flank. Approximately 400 cc were aspirated from each flank. Observations on day 3 post-lipoplasty revealed significant bruising of the flanks extending to the genitalia. Edema was noted throughout the area and the patient was unable to rest without analgesia. On day 10 little change was noted in bruising and edema, but discomfort had diminished. Twenty days post-lipoplasty, minimal yellowing of the skin was observed with pain and edema resolved. Twelve weeks later the patient underwent a 475-cc aspiration of the lower abdomen. In addition to normal post-operative management, the protease-based composition according to the present invention was added to the treatment regiment. Discomfort from the procedure was present only on the first night following surgery. Day 10 examination showed complete resolution of bruising and minimal levels of edema. Examination on day 20 showed complete resolution of all symptoms.

EXAMPLE 5

A 39-year-old female underwent lipoplasty of the lower abdomen, from which approximately 900 cc was aspirated. On days 3 and 10 post-surgery, severe bruising, edema, and discomfort were noted. Analgesics were required for three weeks following the surgery, at the end of which discomfort was minimal but still present. Ten weeks following the first surgery, an additional lipoplasty was performed with 1700 cc removed from the flanks. Post-operative care included the protease-based composition according to the present invention. Examination 3 days post-surgery showed moderate bruising and edema with severe discomfort level. In the day 10 examination, complete resolution of bruising was noted while edema and pain levels were unchanged. Complete resolution of pain was noted by the 20-day post-operative examination with edema present only on deep palpation.

EXAMPLE 6

A 38-year-old female underwent lipoplasty with 1000 cc aspirated from the lower abdomen. Day 3 revealed significant bruising, edema, and discomfort. On day 10 bruising and edema were reduced to moderate levels while discomfort remained unchanged. Some residual bruising and edema were present on day 20, while the discomfort had resolved. Twelve weeks later the patient had 1200 cc aspirated from her flanks. The protease-based composition according to the present invention was added to the normal treatment protocol. Examination on day 3 showed low to moderate bruising and edema. Any discomfort had completely resolved. The day 20 exam revealed resolution of bruising and discomfort while edema was noted only on deep palpation.

EXAMPLE 7

In this example, the protease-based composition according to the present invention was used in a double-blind study of 41 patients undergoing plastic surgery (lipoplasty). Eighteen patients received standard post-operative treatment whereas 23 patients received standard post-operative treatment plus the protease-based composition according to the present invention. All patients were assessed at specified post-operative intervals for ecchymosis (bruising), edema, and pain. The length of time required to resolve all three conditions was significantly reduced in the treatment group receiving the protease-based composition (Lomax, J. E., *The Use of Oral Proteolytic Enzymes in the Post-lipoplasty Patient*, Lipoplasty 15: 10–15 (1998)).

While the invention has been described with reference to preferred embodiments, it will be understood by those of ordinary skill in the art that the invention is not limited thereto. It is obvious that variations in the preferred methods of the present invention may be used and that it is intended that the invention may be practiced otherwise than as specifically described herein. Accordingly, this invention includes all modifications or equivalents encompassed within the spirit and scope of the invention as defined by the appended claims. All publications cited to or referenced herein are incorporated by reference in their entirety.

What is claimed is:

1. A method of treating an alpha$_2$ macroglobulin mediated disease in a mammal in need thereof, comprising: orally administering to the mammal a pharmaceutical composition comprising two or more proteolytic enzymes from a microbial source selected from the group consisting of *Aspergillus oryzae, Aspergillus niger, Aspergillus sojae, Aspergillus flavus, Aspergillus awamori, and Bacillus subtilis*, in an amount from about 20,000 HUT (or equivalent biological activity) to about 550,000 HUT (or equivalent biological activity) per day; wherein the disease is selected from the group consisting of rheumatoid disease, obesity, cachexia, hypertension, cardiovascular disease, dyslipoproteinemia, insulin resistance, non-insulin dependent diabetes, Crohn's disease, dementia, Alzheimer's disease, infection, and soft tissue injury.

2. The method of claim 1, wherein the composition further comprises a plant protease.

3. The method of claim 2, wherein the composition comprises a plant protease in an amount of at least about 50,000 PU (or equivalent biological activity) per day.

4. The method of claim 2, wherein the plant protease is selected from the group consisting of bromelain, and papain, and mixtures thereof.

5. The method of claim 1, wherein the composition is administered in an amount from about 100,000 HUT (or equivalent biological activity) to about 350,000 HUT (or equivalent biological activity) per day.

6. The method of claim 1, wherein the composition further comprises at least one ingredient selected from the group consisting of a vitamin, a mineral, an antioxidant, a bioflavonoid, a proanthocyanidin, a herb, a herbal extract, a plant concentrate, an animal concentrate, and a non-prescription analgesic.

7. A pharmaceutical composition, comprising: about 20,000 HUT (or equivalent biological activity) to about 550,000 HUT (or equivalent biological activity) of two or more microbial proteases from a microbial source selected from the group consisting of *Aspergillus oryzae, Aspergillus niger, Aspergillus sojae, Aspergillus flavus, Aspergillus awamori, and Bacillus subtilis*; and a plant protease in an amount from about 80,000 PU (or equivalent biological activity) to about 1.5 million PU (or equivalent biological activity).

8. The composition of claim 7 further comprising ingredients selected from the group consisting of: (a) from about 15 mg to 100 mg of ascorbic acid, provided by acceptable salts thereof, and mixtures thereof; (b) from about 15 mg to 100 mg of antioxidant bioflavonoids; and (c) from about 2 mg to 15 mg of proanthocyanidins.

9. The composition of claim 7 further comprising ingredients selected from the group consisting of: (a) from about 5 mg to 150 mg of calcium, provided by acceptable salts thereof, and mixtures thereof; and (b) from about 40 mg to 200 mg of trace mineral-rich algae.

10. The composition of claim 7 further comprising an effective amount of an analgesic.

11. The composition of claim 10 wherein said analgesic is selected from the group consisting of acetaminophen, ibuprofen, ketoprofen, salicylates, indomethacin, and mixtures thereof.

12. The composition of claim 10 wherein said analgesic is acetaminophen and said effective amount is from about 65 mg to 325 mg per dosage unit.

13. A method for promoting recovery from soft tissue injury in a patient in need thereof, comprising: orally administering to the patient an effective amount of a composition comprising two or more microbial proteases from a microbial source selected from the group consisting of: *Aspergillus oryzae, Aspergillus niger, Aspergillus sojae, Aspergillus Flavus, Aspergillus awamori, and Bacillus subtilis*, in an amount from about 20,000 HUT (or equivalent biological activity) to about 550,000 HUT (or equivalent biological activity) per day.

14. The method of claim 13 wherein said composition further comprises ingredients selected from the group consisting of: (a) from about 15 mg to 100 mg of ascorbic acid, provided by acceptable salts thereof, and mixtures thereof; (b) from about 15 mg to 100 mg of antioxidant bioflavonoids; and (c) from about 2 mg to 15 mg of proanthocyanidins.

15. The method of claim 13 wherein said composition further comprises ingredients selected from the group consisting of (a) from about 5 mg to 150 mg of calcium, provided by acceptable salts thereof, and mixtures thereof; and (b) from about 40 mg to 200 mg of trace mineral-rich algae.

16. The method of claim 13 wherein the composition further comprises an effective amount of an analgesic.

17. The method of claim 16 wherein said analgesic is selected from the group consisting of acetaminophen, ibuprofen, ketoprofen, salicylates, indomethacin, and mixtures thereof.

18. The method of claim 16 wherein said analgesic is acetaminophen and said effective amount is from about 65 mg to 325 mg per dosage unit.

19. The method of claim 13, further comprising: a plant protease.

20. The method of claim 19, wherein the plant protease is administered in an amount of at least about 50,000 PU (or equivalent biological activity) per day.

* * * * *